(12) United States Patent
Teramoto et al.

(10) Patent No.: US 10,827,988 B2
(45) Date of Patent: Nov. 10, 2020

(54) X-RAY CT APPARATUS

(71) Applicant: Toshiba Medical Systems Corporation, Otawara (JP)

(72) Inventors: Ryuichi Teramoto, Yokohama (JP); Ryo Furukawa, Kawasaki (JP); Kiminori Toya, Kawasaki (JP); Yohei Matsuzawa, Nasushiobara (JP); Masayuki Wakahara, Utsunomiya (JP); Keisuke Oishi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 680 days.

(21) Appl. No.: 15/589,458

(22) Filed: May 8, 2017

(65) Prior Publication Data

US 2017/0325759 A1 Nov. 16, 2017

(30) Foreign Application Priority Data

May 9, 2016 (JP) .................................. 2016-094044
Apr. 26, 2017 (JP) .................................. 2017-087432

(51) Int. Cl.
*A61B 6/04* (2006.01)
*A61B 6/03* (2006.01)
*A61B 6/00* (2006.01)
*A61B 6/08* (2006.01)

(52) U.S. Cl.
CPC ............. *A61B 6/0407* (2013.01); *A61B 6/032* (2013.01); *A61B 6/04* (2013.01); *A61B 6/0457* (2013.01); *A61B 6/08* (2013.01); *A61B 6/4035* (2013.01); *A61B 6/4085* (2013.01); *A61B 6/461* (2013.01); *A61B 6/54* (2013.01); *A61B 6/545* (2013.01)

(58) Field of Classification Search
CPC ......... A61B 6/032; A61B 6/04; A61B 6/0407; A61B 6/0457; A61B 6/08; A61B 6/4035; A61B 6/4085; A61B 6/461; A61B 6/54; A61B 6/545
See application file for complete search history.

(56) References Cited

U.S. PATENT DOCUMENTS

2002/0140699 A1* 10/2002 Miyadai ................ G06T 11/206
                                                                   345/440
2014/0161222 A1   6/2014 Tsuyuki
2017/0303873 A1* 10/2017 Toya ...................... A61G 13/02

FOREIGN PATENT DOCUMENTS

| JP | 3-64998 | 3/1991 |
| JP | 2005-245663 | 9/2005 |
| JP | 2007-136229 | 6/2007 |
| JP | 2008-220647 | 9/2008 |
| JP | 2009-209 | 1/2009 |

(Continued)

*Primary Examiner* — Chih-Cheng Kao
(74) *Attorney, Agent, or Firm* — Oblon, McClelland, Maier & Neustadt, L.L.P.

(57) ABSTRACT

An X-ray computed-tomography (CT) apparatus according to an embodiment includes an X-ray tube, a detector, a table top, and processing circuitry. The X-ray tube generates an X-ray. The detector detects the X-ray. On the table top, a subject is placed. The processing circuitry controls a moving mechanism to move the table top in a longitudinal direction. The processing circuitry displays information indicating magnitude of a vibration that occurs, when each position in the longitudinal direction on the table top is moved to a position intersecting a path of the X-ray, at the position.

17 Claims, 10 Drawing Sheets

(56) References Cited

FOREIGN PATENT DOCUMENTS

| | | |
|---|---|---|
| JP | 2009-268799 | 11/2009 |
| JP | 2010-269066 | 12/2010 |
| JP | 2014-64900 | 4/2014 |

* cited by examiner

FIG.5

|  | POSITION 1 | POSITION 2 | POSITION 3 | ... |
|---|---|---|---|---|
| WEIGHT 1 | AMPLITUDE 11 | AMPLITUDE 12 | AMPLITUDE 13 | ... |
| WEIGHT 2 | AMPLITUDE 21 | AMPLITUDE 22 | AMPLITUDE 23 | ... |
| WEIGHT 3 | AMPLITUDE 31 | AMPLITUDE 32 | AMPLITUDE 33 | ... |
| ⋮ | ⋮ | ⋮ | ⋮ | ... |

FIG.6

| HEIGHT 1 | MOVING AMOUNT 1 | WEIGHT 1 | MOVING SPEED 1 | ATTENUATION TIME 1 |
|---|---|---|---|---|
| HEIGHT 2 | MOVING AMOUNT 2 | WEIGHT 2 | MOVING SPEED 2 | ATTENUATION TIME 2 |
| HEIGHT 3 | MOVING AMOUNT 3 | WEIGHT 3 | MOVING SPEED 3 | ATTENUATION TIME 3 |
| ⋮ | ⋮ | ⋮ | ⋮ | ⋮ |

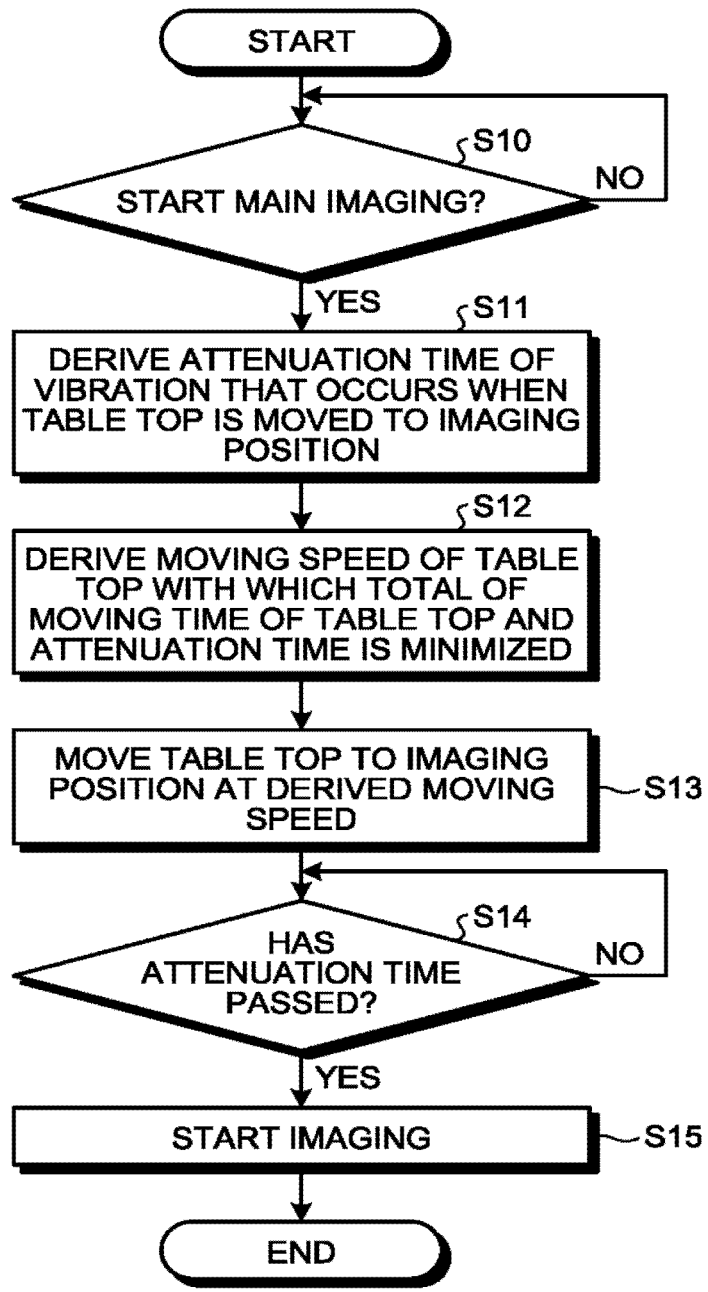

X-RAY CT APPARATUS

CROSS-REFERENCE TO RELATED APPLICATIONS

This application is based upon and claims the benefit of priority from Japanese Patent Application No. 2016-094044, filed on May 9, 2016; and Japanese Patent Application No. 2017-087432, filed on Apr. 26, 2017, the entire contents of which are incorporated herein by reference.

FIELD

An embodiment described herein relates generally to an X-ray computed tomography (CT) apparatus.

BACKGROUND

Conventionally, an X-ray CT apparatus includes a table top on which a subject is placed, and moves the table top on a moving path that intersects a path of an X-ray from an X-ray tube to a detector. Furthermore, when imaging of the subject is performed, the X-ray CT apparatus moves the table top on which the subject is place to an imaging position at which a portion of a subject of imaging intersects an X-ray. In such an X-ray CT apparatus, when moving the table top, vibrations may occur at various positions on the table top, for example, due to the table top and a mechanical structure around the table top, and the like. If imaging is performed in a state in which vibrations are occurring at the portion of a subject of imaging, the image quality of an image to be obtained can be degraded.

BRIEF DESCRIPTION OF THE DRAWINGS

FIG. 5 shows one example of information of a vibration that is stored by storage circuitry according to the present embodiment;

FIG. 6 shows one example of information of an attenuation time stored by the storage circuitry according to the present embodiment;

FIG. 12 is a flowchart showing a processing procedure of main imaging that is performed by the imaging control function according to the present embodiment.

DETAILED DESCRIPTION

An X-ray CT apparatus according to an embodiment includes an X-ray tube, a detector, a table top, and processing circuitry. The X-ray tube generates an X-ray. The detector detects the X-ray. On the table top, a subject is placed. The processing circuitry controls a moving mechanism to move the table top in a longitudinal direction. The processing circuitry displays information indicating magnitude of vibration that occurs at each position when each position on the table top is moved to a position intersecting the path of the X-ray.

An embodiment of the X-ray CT apparatus according to the present application is explained in detail below referring to the accompanying drawings. Note that the embodiment explained below is one example, and the X-ray CT apparatus according to the present application is not limited the following embodiment.

Figure 1:
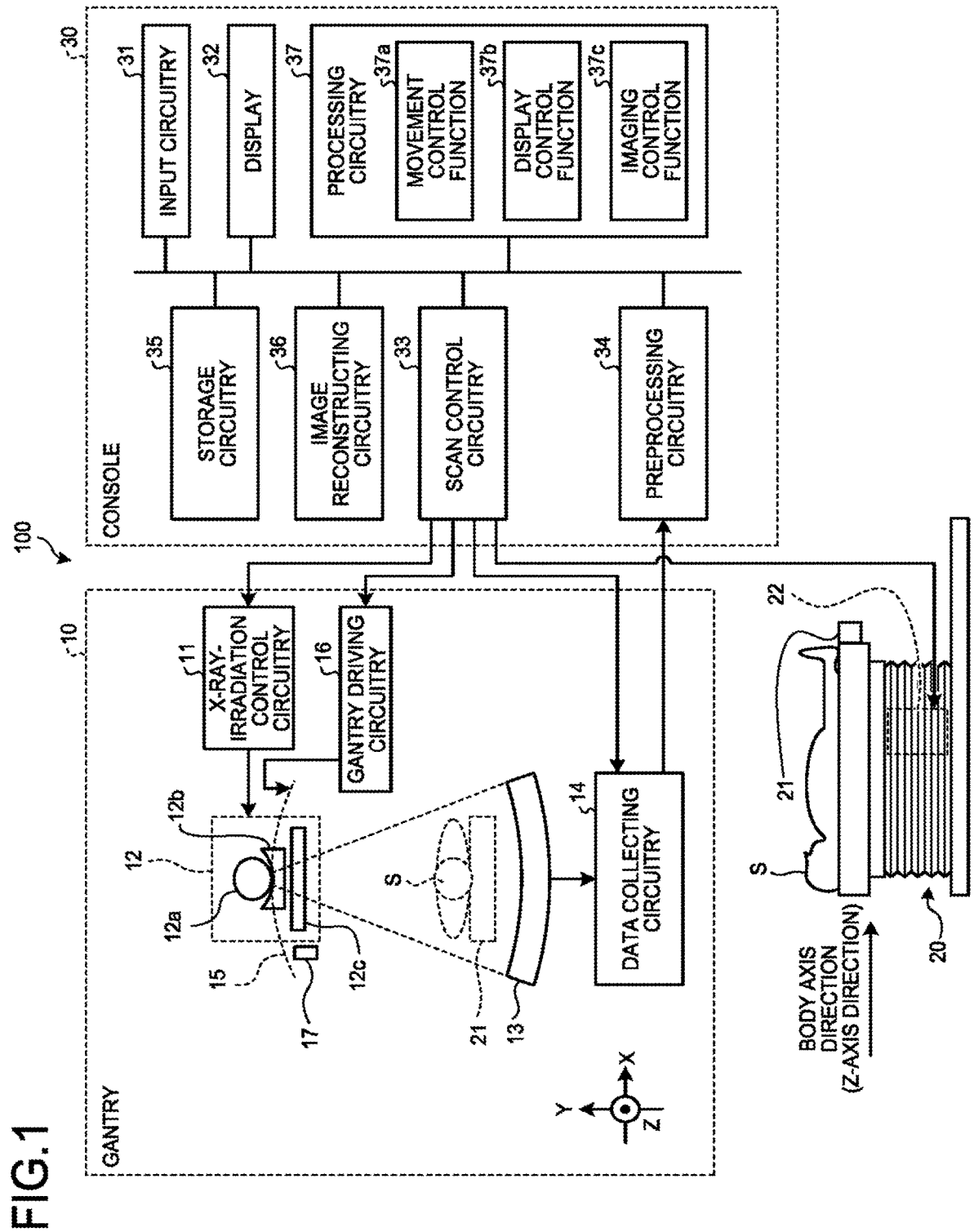
FIG. 1 shows a configuration example of an X-ray CT apparatus according to a present embodiment.

FIG. 1 shows a configuration example of an X-ray CT apparatus according to a present embodiment. For example, as shown in FIG. 1, an X-ray CT apparatus 100 according to the present embodiment includes a gantry 10, a bed 20, and a console 30.

The gantry 10 is a device that irradiates an X-ray to a subject S (patient), and detects an X-ray that has passed through the subject S to output to the console 30. For example, the gantry 10 includes X-ray-irradiation control circuitry 11, an X-ray generating device 12, a detector 13, data collecting circuitry (data acquisition system (DAS)) 14, a rotating frame 15, gantry driving circuitry 16, and a projector 17.

The X-ray generating device 12 generates an X-ray, and irradiates the generated X-ray to the subject S. For example, the X-ray generating device 12 includes an X-ray tube 12a, a wedge 12b, and a collimator 12c.

The X-ray tube 12a generates an X-ray. For example, the X-ray tube 12a is a vacuum tube, and generates an X-ray by a high voltage supplied from a high-voltage generating device not shown. Moreover, the X-ray tube 12a generates an X-ray that radiates in a fan angle and a cone angle.

The wedge 12b is an X-ray filter to adjust an amount of an X-ray that is radiated from the X-ray tube 12a. Specifically, the wedge 12b is a filter through which an X-ray radiated from the X-ray tube 12a passes to be attenuated so that the X-ray to be irradiated to the subject S from the X-ray tube 12a has a predetermined distribution. For example, the wedge 12b is a filter that is obtained by processing aluminum to have predetermined target angle and a predetermined thickness. The wedge is called wedge filter, or bow-tie filter.

The collimator 12c is a slit to narrow an irradiation range of an X-ray, the amount of which has been adjusted by the wedge 12b, under control of the X-ray-irradiation control circuitry 11 described later.

The X-ray-irradiation control circuitry 11 controls the X-ray generating device 12 under control of scan control circuitry 33 described later. For example, the X-ray-irradiation control circuitry 11 controls the high-voltage generating device not shown, and supplies a high voltage to the X-ray tube 12a included in the X-ray generating device 12. Furthermore, the X-ray-irradiation control circuitry 11 adjusts an amount of X-ray to be irradiated to the subject S by adjusting a tube voltage and a tube current to be supplied to the X-ray tube 12a. Moreover, the X-ray-irradiation control circuitry 11 switches the wedge 12b included in the X-ray generating device 11. Furthermore, the X-ray-irradiation control circuitry 11 adjusts an irradiation range (a fan angle or a cone angle) of an X-ray by adjusting an opening degree of the collimator 12c included in the X-ray generating device 12.

The detector 13 detects an X-ray that is generated from the X-ray tube 12a. For example, the detector 13 is a two-dimensional array detector (surface detector) that detects an X-ray that has passed through the subject S, and has rows of detecting devices in which X-ray detectors for multiple channels are arranged are aligned in multiple rows along a body axis direction (a Z-axis direction shown in FIG. 1) of the subject S. Specifically, the detector 13 according to the present embodiment has X-ray detecting devices that are arranged in multiple rows of 320 rows and the like along the body axis direction of the subject S, and is capable of, for example, detecting an X-ray that has passed through the subject S in a wide range, such as a range including a lung and a heart of the subject S.

The rotating frame 15 is a frame that is formed in an annular shape, and supports the X-ray generating device 12 and the detector 13 so as to oppose to each other about the subject S.

The gantry driving circuitry 16 rotates the X-ray generating device and the detector 13 on a circular orbit about the subject in center, by driving the rotating frame 15 to be rotated, under control of the scan control circuitry 33 described later.

The data collecting circuitry 14 collects projection data from detection data of an X-ray detected by the detector 13 under control of the scan control circuitry 33 described later. The data collecting circuitry 14 is also called DAS. For example, the data collecting circuitry 14 performs amplification processing, analog-to-digital (A/D) conversion processing, sensitivity correction processing among channels, and the like on an X-ray-intensity distribution data that is detected by the detector 13, to generate projection data, and transmits the generated projection data to the console 30 described later. The sensitivity correction processing among channels can be performed by preprocessing circuitry 34 described later.

The projector 17 irradiates a visible light beam (laser beam) to the table top 21 on which the subject S is placed. For example, the projector 17 is arranged at an upper part of an opening that is formed in the gantry 10, and to which the table top 21 is inserted, and irradiates a visible light beam downward. A position at which the visible light beam is irradiated on the table top 21 looks brighter than other positions. For example, the position at which the visible light beam is irradiated on the table top 21 is used as a reference for positioning at the time of arranging the subject S on the table top 21.

The bed 20 is a device on which the subject S is placed, and as shown in FIG. 1, includes the table top 21 on which the subject S is placed, and the bed driving device 22. The bed driving device 22 moves the table top 21 in the Z-axis direction, and moves the subject S to the inside of the rotating frame 15. That is, the bed driving device 22 is one example of the moving mechanism to move the table top 21 in the longitudinal direction.

The gantry 10 rotates the rotating frame 15 while continuously moving the table top 21, for example, and performs helical scanning in which the subject S is scanned helically. Alternatively, the gantry 10 performs conventional scanning in which the subject S is scanned in a circular orbit by rotating the rotating frame 15 while the position of the subject S is fixed after the table top 21 is moved. Alternatively, the gantry 10 performs step-and-shoot in which the conventional scanning is performed at more than one imaging place while changing the position of the table top 21 at regular intervals.

The console 30 is a device that accepts an operation of the X-ray CT apparatus 100 by an operator, and that reconstructs CT image data by using projection data collected by the gantry 10. The console 30 includes, as shown in FIG. 1, input circuitry 31, a display 32, scan control circuitry 33, preprocessing circuitry 34, storage circuitry 35, image reconstructing circuitry 36, and processing circuitry 37.

The input circuitry 31 has a mouse, a keyboard, a trackball, a switch, a button, a joystick, and the like used to by an operator of the X-ray CT apparatus 100 to input various kinds of instructions and settings, and transfers information about the instructions and settings accepted from the operator to the processing circuitry 37. For example, the input circuitry 31 accepts an imaging condition of CT image data, a reconstruction condition at the time of reconstructing CT image data, an image processing condition for CT image data, and the like from the operator. Moreover, the input circuitry 31 accepts a specification operation to specify a portion on an image and a predetermined region such as a region of interest.

The display 32 is a monitor that is referred to by an operator, and displays a CT image that is generated from CT image data to an operator, or displays a graphical user interface (GUI) to accept various kinds of instructions and settings and the like from the operator through the input circuitry 31 under control of the processing circuitry 37.

The scan control circuitry 33 controls collection processing of projection data in the gantry 10 by controlling operation of the X-ray-irradiation control circuitry 11, the gantry driving circuitry 16, the data collecting circuitry 14, and the bed driving device 22, under control of the processing circuitry 37. For example, the scan control circuitry 33 controls to perform imaging to collect a scano-image that is used in positioning of an imaging region imaged in main imaging. That is, the scano-image is one example of a positioning image of a subject. Furthermore, for example, the scan control circuitry 33 controls collection processing of projection data in the main imaging to collect images to be used for diagnosis.

For example, the scan control circuitry 33 images a two-dimensional scano-image by performing continuous imaging with the X-ray tub 12a fixed at a position of 0 degree (position in a front direction for the subject S) while moving the table top 21 at a constant speed. Alternatively, the scan control circuitry 33 acquires a two-dimensional scano-image by repeating intermittent imaging synchronizing with movement of the table op, with the X-ray tube 12a fixed at the position of 0 degree, while moving the table top 21 intermittently. The scan control circuitry 33 can take a scano-image not only from the front direction of the subject S, but also from any direction (for example, a side direction, and the like).

The preprocessing circuitry 34 performs correction processing, such as logarithmic conversion processing, offset correction, sensitivity correction, and beam hardening correction, on the projection data generated by the data collecting circuitry 14, to generate corrected projection data. Specifically, the preprocessing circuitry 34 generates corrected projection data for each of the projection data of the scano-image that is generated by the data collecting circuitry 14 and projection data that is collected in the main imaging, to store in the storage circuitry 35.

The storage circuitry 35 stores projection data generated by the preprocessing circuitry 34. Specifically, the storage circuitry 35 stores projection data of a scano-image that is generated by the preprocessing circuitry 34, and projection data for diagnosis collected in the main imaging. Moreover, the storage circuitry 35 stores a CT image that is generated by the image reconstructing circuitry 36 described later, and the like. Furthermore, the storage circuitry 35 stores, as necessary, a processing result by the processing circuitry 37 described later.

The image reconstructing circuitry 36 reconstructs CT image data by using the projection data stored in the storage circuitry 35. Specifically, the image reconstruction circuitry 36 reconstructs CT image data from each of the projection data of the scano-image and the projection data of an image used for diagnosis. Various methods are available as a reconstruction method, and the back projection processing is one, for example. Moreover, as the back projection processing, for example, back projection processing by filtered back projection (FBP) can be applied. Alternatively, the image reconstructing circuitry 36 can reconstruct CT image data by using a method of successive approximation. Furthermore, the image reconstructing circuitry 36 generates various CT images by performing various kinds of image processing on CT image data. The image reconstructing circuitry 36 stores the reconstructed CT image data, and the CT image that is generated by various kinds of image processing in the storage circuitry 35.

The processing circuitry 37 performs overall control of the X-ray CT apparatus 100 by controlling operation of the gantry 10, the bed 20, and the console 30. Specifically, the processing circuitry 37 controls CT scanning performed in the gantry 10 by controlling the scan control circuitry 33. Moreover, the processing circuitry 37 controls the image reconstruction processing and the image generation processing in the console 30 by controlling the image reconstructing circuitry 36. Furthermore, the processing circuitry 37 controls to display various kinds of CT images stored in the storage circuitry 35 on the display 32.

As above, the entire configuration of the X-ray CT apparatus according to the present embodiment has been explained.

In the X-ray CT apparatus 100 thus configured, there is a case in which a vibration occurs at each position on the table top 21, for example, due to the table top 21, a mechanical structure around the table top 21, and the like when the table top 21 is moved. If imaging is performed in a state in which a vibration is occurring at a portion of a subject of imaging, the image quality of an image to be obtained can be degraded.

Generally, a bed that is provided in an X-ray CT apparatus has a cantilever structure supporting one end of a table top on which a subject is placed, and a contact state between a support point and the table top can change due to a distance between support points and flexure of the table top. There is an inflection point at which a state of balance in this contact state of the support point and the table top, and it is supposed that a vibration of the table top increases when passing through this inflection point. When imaging is performed in a state in which the position of a portion of a subject of imaging on the table top is vibrating, the image quality of an image to be obtained can be degraded.

For such a reason, the X-ray CT apparatus 100 according to the present embodiment is configured to be capable of supporting appropriate positioning of a subject on the table top taking a vibration occurring in the table top into account. In the following, such a configuration of the X-ray CT apparatus 100 is explained in more detail.

For example, as shown in FIG. 1, the processing circuitry 37 includes a movement control function 37a, a display control function 37b, and an imaging control function 37c. The processing circuitry 37 is one example of processing circuitry described in claims.

For example, the processing circuitry 37 is implemented by a processor. Moreover, the respective functions of the movement control function 37a, the display control function 37b, and the imaging control function 37c are stored in the storage circuitry 35 in a form of computer-executable program. The processing circuitry 37 implements the functions corresponding to the respective programs by reading and executing the respective programs from the storage circuitry 35. In other words, the processing circuitry 37 that has read the respective programs is to have the respective functions shown in the processing circuitry 37 in FIG. 1.

The movement control function 37a moves the table top 21 on a moving path that intersects a path of an X-ray from the X-ray tube 12a to the detector 13. Specifically, the movement control function 37a moves the table top 21 on the moving path by controlling the bed driving device 22. That is, the movement control function 37a controls the moving mechanism to move the table top 21 in the longitudinal direction.

Figure 2:
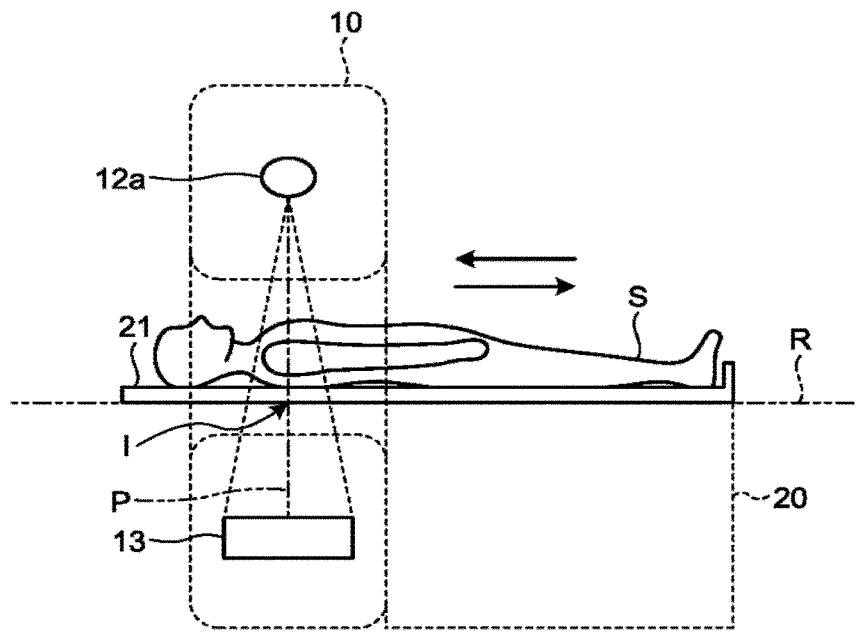
FIG. 2 shows movement of a table top by a movement control function according to the present embodiment.

FIG. 2 shows movement the table top 21 by the movement control function 37a according to the present embodiment. For example, as shown in FIG. 2, the movement control function 37a moves the table top 21 in a direction toward the gantry 10 from the bed 20, and in a direction toward the bed 20 from the gantry 10, on a moving path R that passes between the X-ray tube 12a and the detector 13 that are arranged in the gantry 10. For example, the moving path is set to intersect a path P of an X-ray that travels from a center of the X-ray tube 12a to a center of the detector 13 at a right angle at position I on the moving path R.

As described above, when thus moving the table top 21, there is a case in which a vibration occurs at each position on the table top 21, for example, due to the table top 21 and the mechanical structure around the table top, and the like.

Figure 3:
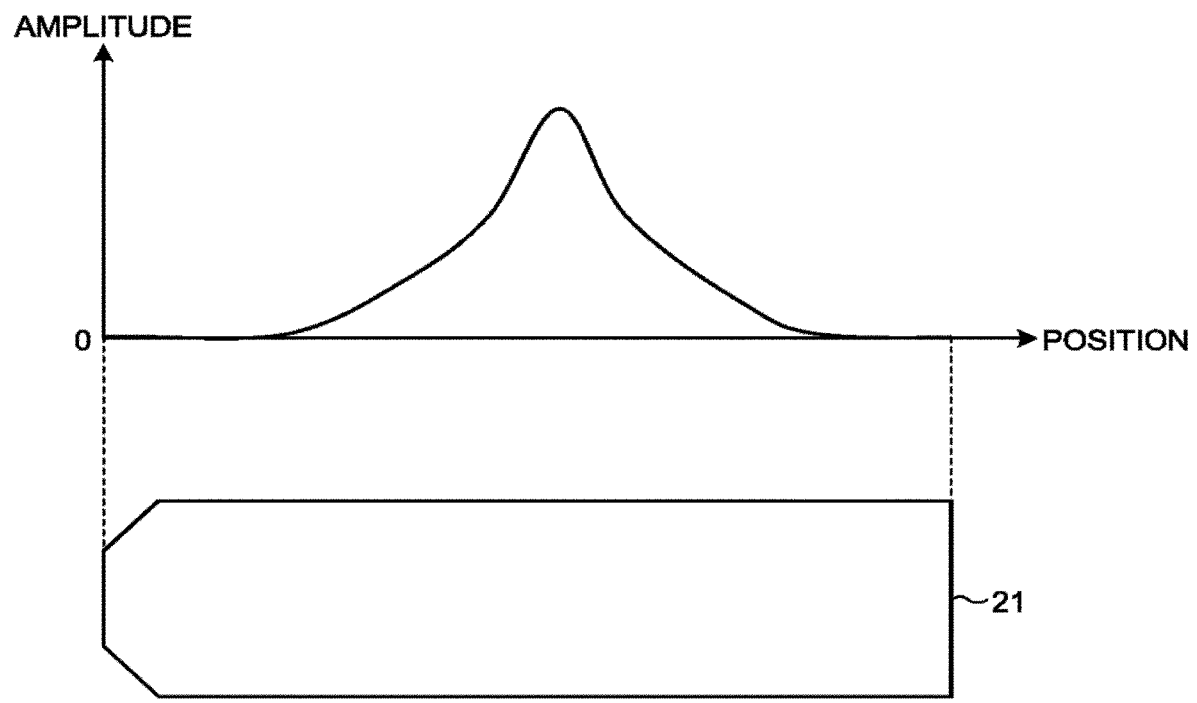
FIG. 3 shows one example of a vibration that occurs at each position on the table top according to the present embodiment.

FIG. 3 shows one example of a vibration that occurs at each position on the table top 21 according to the present embodiment. A figure shown on an upper side of FIG. 2 indicates the magnitude of vibration that occurs on the table top 21 when the table top 21 is continuously moved in the direction toward the gantry 10 from the bed 20. In the figure shown on the upper side of FIG. 3, a horizontal axis indicates each position when a position at the end of the table top 21 is 0, and a vertical axis indicates the magnitude of amplitude of the vibration that occurs at each position on the table top 21 at position I shown in FIG. 2. Furthermore, a figure shown on a lower side of FIG. 3 indicates a state of the table top 21 viewed from above, matching a position in a longitudinal direction to the position in the horizontal axis in the figure shown on the upper side.

For example, as shown in FIG. 3, when the table top 21 is moved continuously in the direction toward the gantry 10 from the bed 20, there is a case in which a large vibration occurs at one position on the table top 21 compared to other positions. FIG. 3 shows an example in which a vibration that is maximized near the center of the table top 21 in the longitudinal direction has occurred. If imaging is performed placing a portion of a subject of imaging at a position at which a large vibration occurs as above, the image quality of an image to be obtained can be degraded.

Referring back to FIG. 1, the display control function 37b displays information indicating the magnitude of vibration that occurs at each position when the position on the table top 21 is moved to a position intersecting the path of an X-ray on the moving path. That is, the display control function 37b displays information indicating the magnitude of vibration that occurs, when each position in the longitudinal direction on the table top 21 is moved to a position intersecting the path of an X-ray, at the position. Specifically, the display control function 37b displays the information indicating the magnitude of vibration on the display 32.

For example, the display control function 37b displays a table top image that shows the shape of the table top 21, and displays the information indicating the magnitude of vibration associating with each position on the table top image. That is, the table top image is one example of a simulation image of the table top 21.

Figure 4:
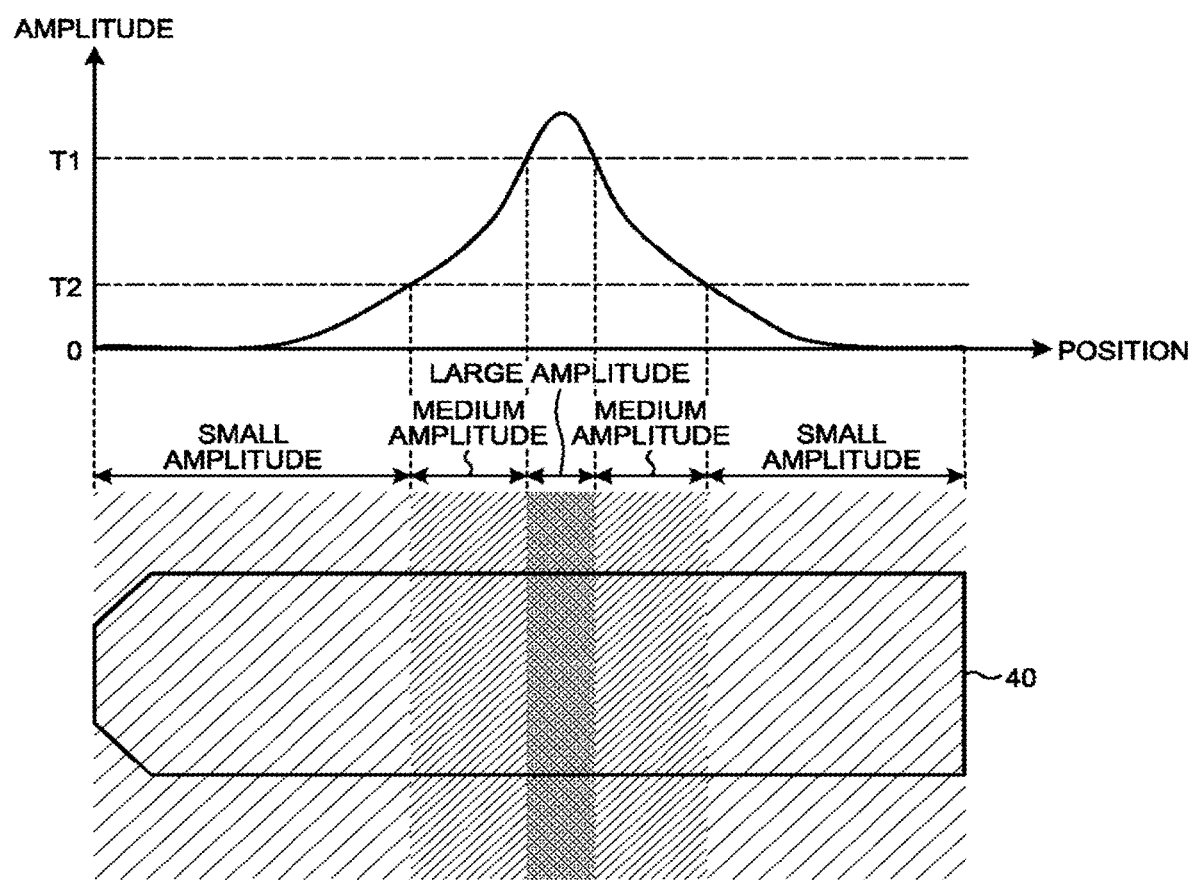
FIG. 4 shows one example of information that is displayed by a display control function according to the present embodiment.

FIG. 4 shows one example of the information that is displayed by the display control function 37b according to the present embodiment. FIG. 4 shows the same example as FIG. 3. For example, as shown on a lower side of FIG. 4, the display control function 37b displays a table top image 40 that expresses the shape of the table top 21. Furthermore, the display control function 37b colors the table top image 40 in different colors according to the magnitude of vibration that occurs at each position of the table top 21.

For example, as shown in FIG. 4, the display control function 37b divides the amplitude of vibration that occurs at each position on the table top 21 into three ranges using two thresholds T1 and T2 (T1>T2). For example, the display control function 37b determines a range of amplitude≥T1 as "large amplitude", a range of T1>amplitude≥T2 as "medium amplitude", and a range of amplitude<T2 as "small amplitude". The display control function 37b colors the respective ranges of amplitude in different colors in the table top image 40.

Although an example of dividing the amplitude into three ranges has been explained herein, embodiments are not limited thereto. For example, the display control function 37b can divide the amplitude into four or more ranges, or can color each position according to the magnitude of amplitude. Alternatively, the display control function 37b can use different patterns, not using different colors according to the magnitude of amplitude.

As described, the display control function 37b displays the information indicating the magnitude of vibration that occurs at each position when the position on the table top 21 is moved to a position intersecting the path of an X-ray, and a radiologist or the like refers to the displayed information when positioning a subject on the table top 21, thereby enabling to position the subject such that a portion of a subject of imaging is placed at a position at which a vibration is small.

As described, the display control function 37b displays information indicating the magnitude of vibration, associating with the simulation image of the table top 21.

Moreover, the display control function 37b displays, according to an imaging condition, information indicating the magnitude of vibration that occurs when imaging is performed based on the imaging condition.

For example, the display control function 37b displays, according to a weight of a subject, information indicating the magnitude of vibration that occurs when a subject of the weight is placed on the table top 21.

Specifically, for example, the display control function 37b displays the information indicating the magnitude of vibration based on a measurement result obtained by measuring vibrations while moving the table top 21 with various weights of a subject. In this case, for example, the storage circuitry 35 stores information in which each position when the position at the end of the table top 21 is 0 as shown in FIG. 3 is associated with the magnitude of amplitude of vibration that occurs at each position on the table top 1 at position I shown in FIG. 2, for each weight of a subject.

FIG. 5 shows one example of information of a vibration that is stored by the storage circuitry 35 according to the present embodiment. For example, as shown in FIG. 5, the storage circuitry 35 stores information in which respective positions (position 1, position 2, position 3, . . . ) on the table top 21 and the magnitudes of amplitude of vibration that occurs at the respective positions (amplitude 11, amplitude 12, amplitude 13, . . . ) are associated per weight of a subject (weight 1, weight 2, weight 3, . . . ). This information is generated based on a measurement result and stored in the storage circuitry 35 in advance, before the X-ray CT apparatus 100 is started to be used (for example, at the time of shipment, installation, or the like of the X-ray CT apparatus 100).

The display control function 37b refers to the information of vibration that is stored in the storage circuitry 35, and acquires information corresponding to the weight of a subject set as a part of imaging condition. The display control function 37b then displays information indicating the magnitude of vibration that occurs at each position on the table top 21 based on the acquired information.

When the relationship between the weight of a subject and amplitude of vibration that occurs at each position of the table top 21 can be defined by a function, for example, the display control function 37b can derive the magnitude of vibration that occurs at each position of the table top 21 by using the function. In this case, the display control function 37b calculates an amplitude of vibration that occurs at each position of the table top 21 from a weight of a subject set as a part of the imaging condition by using the function. The display control function 37b then displays information indicating the magnitude of vibration that occurs at each position on the table top 21 based on a result of calculation.

As described, the display control function 37b displays the information indicating the magnitude of vibration that occurs according to a weight of a subject when a subject of the weight is placed on the table top 21, thereby enabling to perform positioning of a subject further appropriately corresponding to individual subjects, even when vibrations that occur on the table top 21 vary depending on the weight of a subject.

Although the example in which the path of an X-ray is a straight path toward the center of the detector 13 from the center of the X-ray tube 12a has been shown in FIGS. 2 to 5, embodiments are not limited to thereto.

Generally, an X-ray that is emitted from the X-ray tube 12a radiates and enters the detector 13. Therefore, for example, the path of an X-ray can be a path having a width in the longitudinal direction of the table top 21.

In this case, for example, the display control function 37b displays information indicating a mean value of the magnitude of vibrations that occur at respective positions in the longitudinal direction within a range in which the table top 21 and the path of the X-ray intersect with each other, as the information indicating the magnitude of vibration that occurs at each position in the longitudinal direction of the table top 21. The mean value displayed herein is a mean value of the magnitude of vibrations that occur at respective positions in the range when the respective positions on the table top 21 are moved to a position at the center in the longitudinal direction within the range in which the table top 21 and trio path of an X-ray intersect with each other.

Furthermore, in this case, the storage circuitry 35 stores information in which each position in the longitudinal direction on the table top 21 and the mean value described above are associated with each other per weight of a subject.

Moreover, for example, the display control function 37b can display information indicating the magnitude of vibration according to an imaging condition relating to an orientation of the subject in the longitudinal direction when the subject is placed on the table top 21.

For example, the imaging condition relating to an orientation of a subject in this example includes an inserting orientation of a subject when the subject is inserted into the opening of the gantry 10. For example, as the inserting orientation of a subject, "head first" indicating that the subject is inserted from the head into the opening of the gantry 10, or "foot first" indicating that the subject is inserted from feet into the opening of the gantry 10 is set. It is considered that the magnitude of vibration occurring in the table top 21 varies between a case of imaging in head first and a case of imaging in foot first, as the arrangement of the subject is different.

Furthermore, for example, the imaging condition relating to an orientation of a subject includes whether an accessory to be attached at an end portion in the longitudinal direction of the table top 21 is used. For example, there is a case that the head or feet of a subject are off an edge of the table top 21 depending on a position of a portion subject of imaging, the height of the subject, or the like. In such a case, an accessory such as a headrest to support the head and a footrest to support the feet can be attached at an end portion in the longitudinal direction of the table top 21. When the accessory is attached to the table top 21, it is considered that the magnitude of vibration that occurs in the table top 21 varies as the arrangement of a subject on the table top 21 is different from when the accessory is not used.

As described, the magnitude of vibration that occurs in the table top 21 is considered to vary according to the imaging condition relating to an orientation of a subject.

Therefore, for example, the display control function 37b displays information indicating the magnitude of vibration based on an actual measurement result that is obtained by measuring a vibration of the table top 21 while changing the imaging condition relating to an orientation of a subject. In this case, for example, the storage circuitry 35 stores information in which each position relative to the position at the end of the table top 21 as 0 as shown in FIG. 3 and the magnitude of amplitude of vibration that occurs at each position on the table top 21 at position I shown in FIG. 2 are associated, per imaging condition relating to an orientation of a subject.

For example, the storage circuitry 35 stores information in which each position (position 1, position 2, position 3, . . . ) on the table top 21 and the magnitude of amplitude (amplitude 11, amplitude 12, amplitude 13, . . . ) of vibration that occurs at each position are associated with each other for each of cases of a case of head first with a headrest, a case of foot first with a footrest, a case of head first with a footrest, a case of foot first with a headrest, a case of Head first without an accessory, and a case of foot first without an accessory. This information is generated based on an actual measurement result and stored in the storage circuitry 35 in advance before the X-ray CT apparatus 100 is started to be used (for example, at the time of shipment, installation, or the like of the X-ray CT apparatus 100) similarly to the case of storing the information per weight of a subject.

The display control function 37b refers to the information of vibration stored in the storage circuitry 35, and acquires information relating to an orientation of a subject set as a part of the imaging condition. The display control function 37b then displays information indicating the magnitude of vibration that occurs at each position on the table top 21 based on the acquired information. In this case also, the display control function 37b can derive the magnitude of vibration that occurs at each position on the table top 21 by using a function.

Moreover, for example, the display control function 37b can display information indicating the magnitude of vibration according to the imaging condition relating to both a weight of a subject and an orientation of a subject. In this case, the storage circuitry 35 stores the information per weight shown in FIG. 5 per imaging condition relating to an orientation of a subject.

As described, the display control function 37b displays, according to an imaging condition, information indicating the magnitude of vibration that occurs when imaging is performed based on the imaging condition, thereby enabling more appropriate positioning of a subject even when the vibration that occurs in the table top 21 varies according to the imaging condition.

Furthermore, for example, the display control function 37b further displays a subject image that expresses the shape of a subject including a portion of a subject of imaging, positioning over a table top image. For example, the display control function 37b displays a simulation image in which the shape of a subject is expressed in a simulated manner so that a portion of a subject of imaging is arranged at a position at which the magnitude of vibration on the table top 21 is smaller than a predetermined value when the subject is positioned on the table top 21 by a radiologist or the like. Moreover, for example, the display control function 37b displays a scans-image as a subject image after the scano-image of the subject is imaged for positioning of an imaging region in which imaging is performed in the main imaging. The display of the subject image to be performed by the display control function 37b is explained in detail later.

Referring back to FIG. 1, the imaging control function 37c derives an attenuation time required until the magnitude of vibration that occurs at a position at which an X-ray intersects on the table top 21 when the table top 21 is moved to an imaging position becomes smaller than a predetermined value, and controls imaging based on the attenuation time. Specifically, the imaging control function 37c starts imaging by controlling the scan control circuitry 33 and the movement control function 37a.

For example, the imaging control function 37c controls imaging based on a measurement result obtained by measuring the attenuation time of vibration, moving the table top 21 while changing a height of the table top 21, a moving amount of the table top 21, a weight of a subject, and a moving speed of the table top 21. In this case, for example, the storage circuitry 35 stores information in which the height of the table top 21, the moving amount of the table top 21, the weight of a subject, and the moving speed of the table top 21 are associated with the attenuation time required until the amplitude of vibration that occurs at each position on the table top 21 at position I shown in FIG. 2 becomes smaller than a predetermined value.

FIG. 6 shows one example of the information of the attenuation time stored by the storage circuitry 35 according to the present embodiment. For example, as shown in FIG. 6, information in which a height (height 1, height 2, height 3, . . . ), a moving amount (moving amount 1, moving amount 2, moving amount 3, . . . ), a weight of a subject (weight 1, weight 2, weight 3, . . . ), and a moving speed of the table top (moving speed 1, moving speed 2, moving speed 3, . . . ) are associated with an attenuation time (attenuation time 1, attenuation time 2, attenuation time 3, . . . ) is stored. The information is generated in advance based on an actual measurement result, and stored in the storage circuitry 35 before the X-ray CT apparatus 100 is started to be used (for example, at the time of shipment, installation, or the like of the X-ray CT apparatus 100).

Furthermore, for example, the imaging control function 37c controls the moving speed of the table top 21 so that a total of a moving time required until the table top 21 is moved to an imaging position and an attenuation time of vibration is minimized. First, the imaging control function 37c refers to the information of an attenuation time stored in the storage circuitry 5, and acquires information corresponding to the height of the table top 21, the moving amount of the table top 21, and the weight of a subject set as a part of an imaging condition. Thereafter, the imaging control function 37c calculates the moving time of the table top from the moving amount of the table top 21 and the moving speed of the table top 21, and calculates the total of the calculated moving time and the attenuation time, for each of the acquired information. The imaging control function 37c identifies information for which the total of the calculated moving time and the attenuation time is minimized, and instructs the movement control function 37a to move the table top 21 at a moving speed in the identified information.

When a relationship among a height of the table top 21, a moving amount of the table top 21, a weight of a subject, and a moving speed of the table top 21 with which a total of a moving time of the table top and an attenuation time is minimized can be defined by a function, the display control function 37b can derived the moving speed of the table top 21 by using the function. In this case, the display control function 37b calculates a moving speed of the table top 21 from a height of the table top 21, a moving amount of the table top 21, a weight of a subject set as a part of an imaging condition, by using the function. The display control function 37b then instructs the movement control function 37a to move the table top 21 at the calculated moving speed.

As described, the imaging control function 37c controls a moving speed of the table top 21 so that a total of a moving time required until the table top 21 is moved to an imaging position and an attenuation time of vibration minimized, thereby enabling to set an optimal imaging time taking a vibration that occurs on the table top 21 into account.

The imaging control function 37c then starts imaging at a point when the calculated attenuation time has passed after the table top 21 is moved to the imaging position. At this time, specifically, the imaging control function 37c starts the imaging by controlling the scan control circuitry 33. The control of imaging that is performed by the imaging control function 37c is explained in detail later.

In the following, the processing performed by the display control function 37b and the imaging control function 37c described above is explained in more detail by referring to a flowchart.

Figure 7:
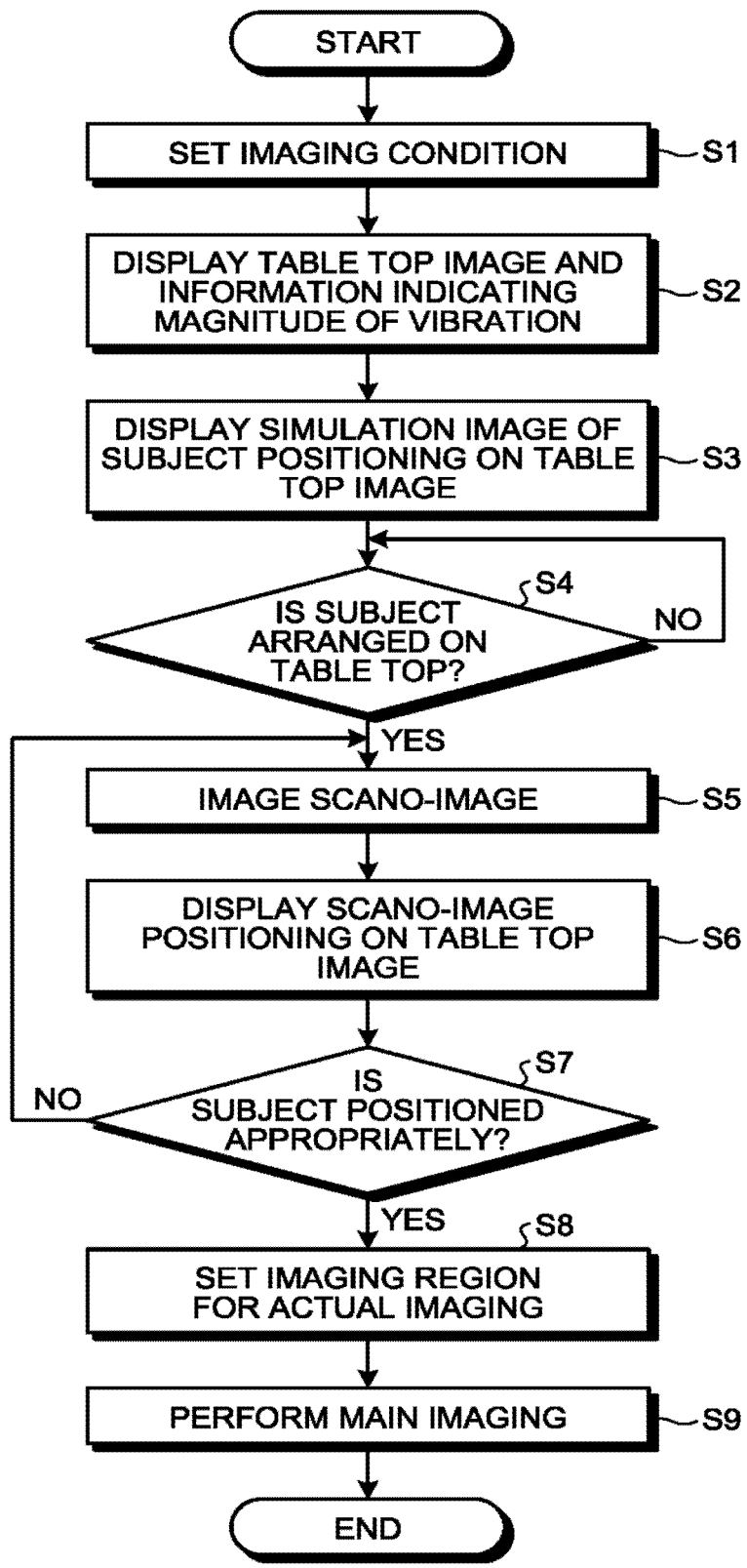
FIG. 7 is a flowchart showing a processing procedure of processing that is performed by a display control function and an imaging control function according to the present embodiment.

FIG. 7 is a flowchart showing a processing procedure of the processing that is performed by the display control function 37b and the imaging control function 37c according to the present embodiment.

For example, as shown in FIG. 7, first, the imaging control function 37c accepts an input of information relating to an imaging condition from an operator through the input circuitry 31, and sets the imaging condition based on the accepted information (step S1). The imaging condition set herein includes a weight of a subject, a height of a subject, a height of the table top 21, a moving amount of the table top 21, an imaging condition relating to an orientation of a subject, and the like.

Thereafter, the display control function 37b displays the table top image 40 expressing the shape of the table top 21, and information indicating a magnitude of vibration that occurs at each position of the table top 21 (step S2). Furthermore, the display control function 37b further displays a simulation image of the subject, positioning over the table top image 40, so that a portion of a subject of imaging is arranged at a position at which the magnitude of vibration on the table top 21 is smaller than a predetermined value (step S3).

Figure 8A:
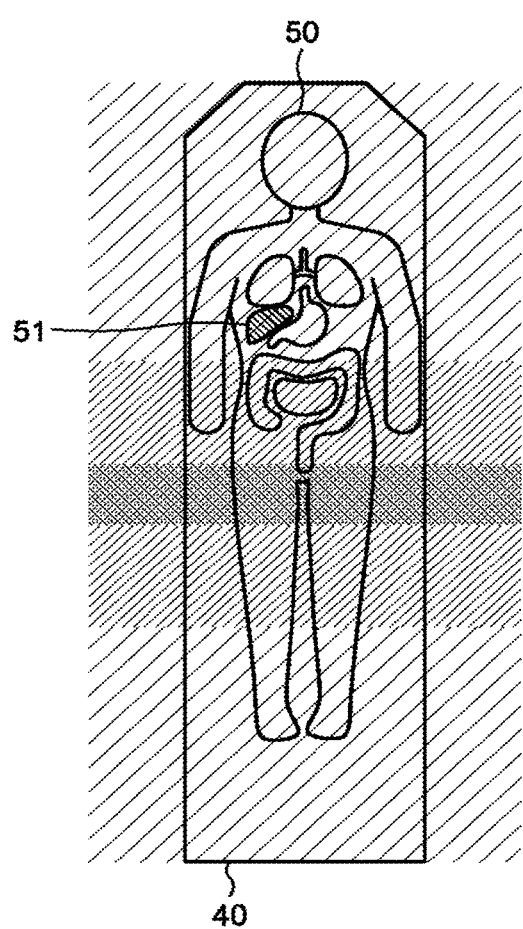
FIGS. 8A to 9B show one example of a display of a simulation image by the display control function according to the present embodiment.

FIGS. 8A to 9B show one example of a display of the simulation image by the display control function 37b according to the present embodiment. FIGS. 8A to 9B show an example in which a magnitude of vibration that occurs at each position on the table top 21 is displayed by dividing the magnitude into three ranges of "small amplitude", "medium amplitude", and "large amplitude" as explained referring to FIG. 4. Moreover, FIGS. 8A and 8B shows an example in which there is one position at which a vibration becomes significantly large on the table top 21 as shown in FIG. 3 and FIG. 4, and FIGS. 9A and 9B show an example in which there are two positions at which a vibration becomes significantly large on the table top 21.

FIG. 8A shows an example in which a portion of a subject of imaging is liver and a direction of a subject set as a part of an imaging condition is HF (head first). In this case, for example, as shown in FIG. 8A, the display control function 37b displays a simulation image 50 such that a head of a subject is arranged on an end side on the table top image 40. Moreover, the display control function 37b displays the simulation image 50, positioning it over the table top image 40 such that a portion 51 of the liver included in the simulation image 5C of a subject is arranged within a range of "small vibration". At this time, for example, the display control function 37b arranges the simulation image 50 such that the portion 51 of the liver is arranged within the range of "small vibration" and at a position close to a center of the table top 21 as much as possible.

Figure 8B:
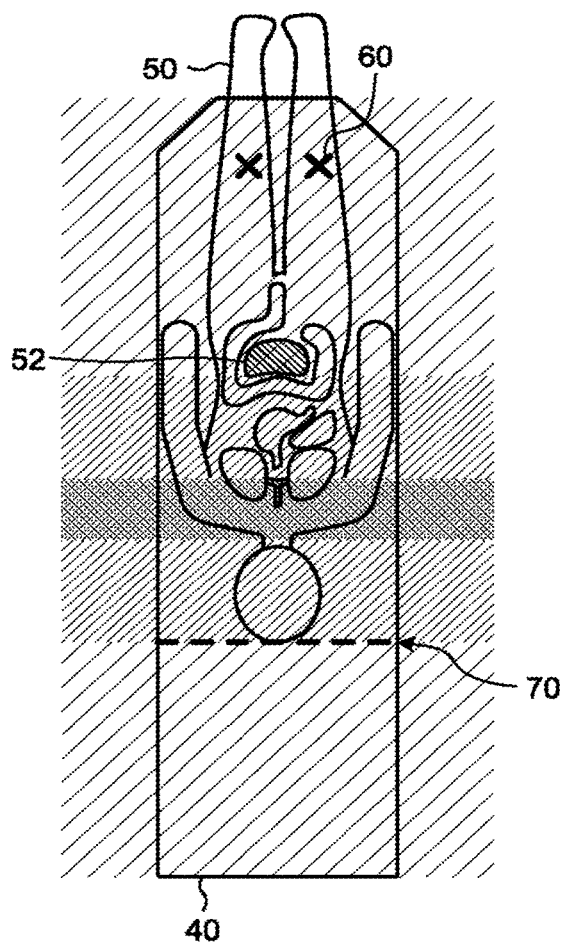

Furthermore, FIG. 8B shows an example in which a portion of a subject of imaging is small intestine, and a direction of a subject set as a part of an imaging condition is FF (foot first). In this case, for example, as shown in FIG. 8B, the display control function 37b displays the simulation image 50 such that legs of a subject are arranged on the end side on the table top image 40. Moreover, the display control function 37b displays the simulation image 50 over the table top image 40 positioning it such that a portion 52 of the small intestine included in a range of "small vibration". At this time, for example, the display control function 37b arranges the simulation image 50 such that the portion 52 of the small intestine is arranged within a range of "small vibration" and at a position close to a center of the table top 21 as much as possible, similarly to the example shown in FIG. 8A.

As described, the display control function 37b displays the simulation image 50 of a subject such that a portion of a subject of imaging at a position at which the magnitude of vibration is smaller than a predetermined value on the table top 21, positioning over the table top image 40, thereby further facilitating positioning of a subject such that a portion of a subject of imaging is arranged at a position at which a vibration is small, when positioning a subject on the table top 21 by a radiologist or the like.

When a part of a subject is off an edge of the table top 21 when the simulation image 50 is positioned over the table top image 40, it is displayed such that the corresponding part recognized on the simulation image 50. For example, as shown in FIG. 8B, when legs of a subject are off an edge of the table top 21, the display control function 37b displays a graphic 60 at a position of the legs.

As described, by visualizing a part that is off an edge of the table top 21 in a recognizable manner on the simulation image 50 by the display control function 37b, it is possible to encourage a radiologist or the like to cope with the part being off the edge of the table top 21, for example, by having legs bent when the legs of a subject are off an edge of the table top 21, and the like.

Figure 9A:
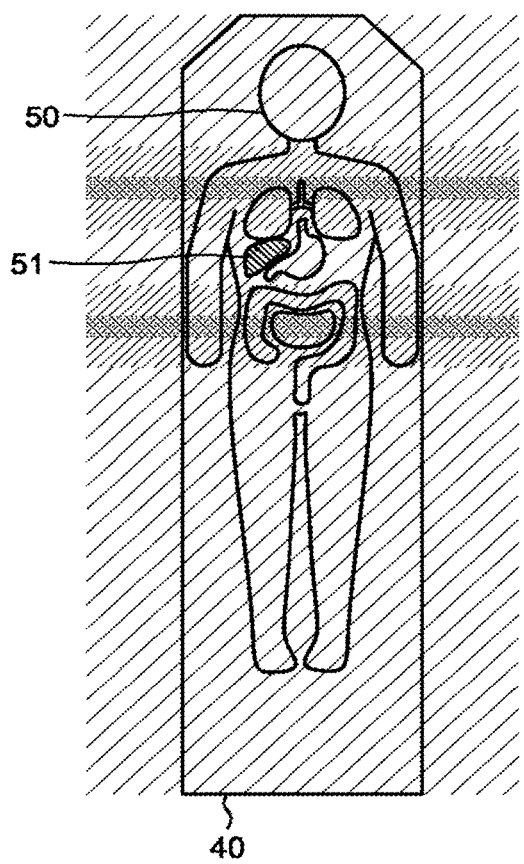
Figure 9B:
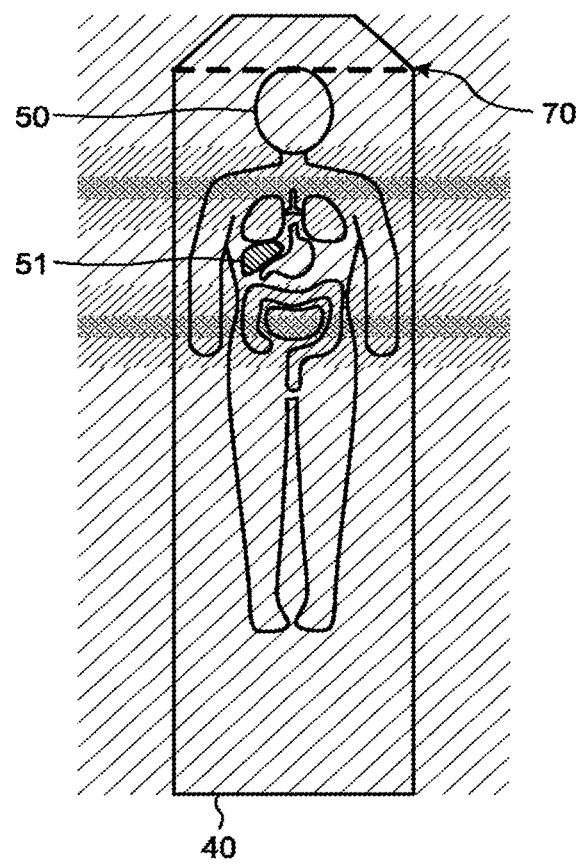

Moreover, for example, the display control function 37b displays the simulation image 50 by changing the size thereof according to a height of a subject. For example, FIGS. 9A and 9B show an example in which a portion of a subject of imaging is liver, and the direction of the subject set as a part of an imaging condition is HF (head first). FIG. 92 shows an example in which the height of a subject is short compared to FIG. 9A.

In this case, for example, the display control function 37b displays the simulation image 50 such that the head of the subject is arranged on the end side on the table top image 40 as shown in FIGS. 9A and 9B. Furthermore, the display control function 37b arranges the simulation image 50 such that the portion 51 of the liver is arranged within range of "small vibration" and at a position close to a center of the table top as much as possible, similarly to the example shown in FIG. 8A.

Moreover, for example, the display control function 37b displays the simulation image 50 by changing the size thereof according to the height of a subject set as a part of an imaging condition, as shown in FIGS. 9A and 9B. Specifically, when the height of the subject is taller than a predetermined reference height, the display control function 37b enlarges and displays the simulation image 50 that has been generated in a size matching the reference height, according to a ratio between the height of the subject and the reference height. On the other hand, when the height of the subject is shorter than the reference height, the display control function 37b reduces and displays the simulation image 50 that has been generated in the size matching the reference height, according to a ratio between the height of the subject and the reference height.

As described, by displaying the simulation image 50 changing the size thereof according to the height of a subject, it is possible to present a positional relationship between the subject and the table top 21 more appropriately to a radiologist or the like.

Furthermore, for example, the display control function 37b further displays information indicating a position to be a reference of positioning of a subject when the subject is to be placed on the table top 21. For example, as shown in FIGS. 5B and 9B, the display control function 37b displays a graphic 70 at a position corresponding to a mark that is marked on the table top 21 in advance.

Although the example of displaying the graphic 70 that indicates a position of a mark that is marked on the table top 21 in advance as information indicating a position to be a reference for positioning of a subject has been explained herein, embodiments are not limited thereto. For example, the display control function 37b can display a graphic that indicates a position at which a visible light beam is irradiated on the table top 21 by the projector 17.

As described, by displaying information that indicates a position to be a reference for positioning of a subject when the subject is to be placed on the table top 21 by the display control function 37b, it enables a radiologist or the like to position a subject more accurately.

As described above, the display control function 37b displays the information indicating the magnitude of vibration, associating with the simulation image that expresses the shape of a subject in a simulated manner.

Referring back to FIG. 7, after a subject is placed on the table top 21 by a radiologist or the like (step S4: YES), the imaging control function 37c images a scano-image in response to a start instruction from an operator (step S5).

Thereafter, the display control function 37b displays the scano-image of the subject positioning on the table top image 40 (step S6).

Figure 10A:
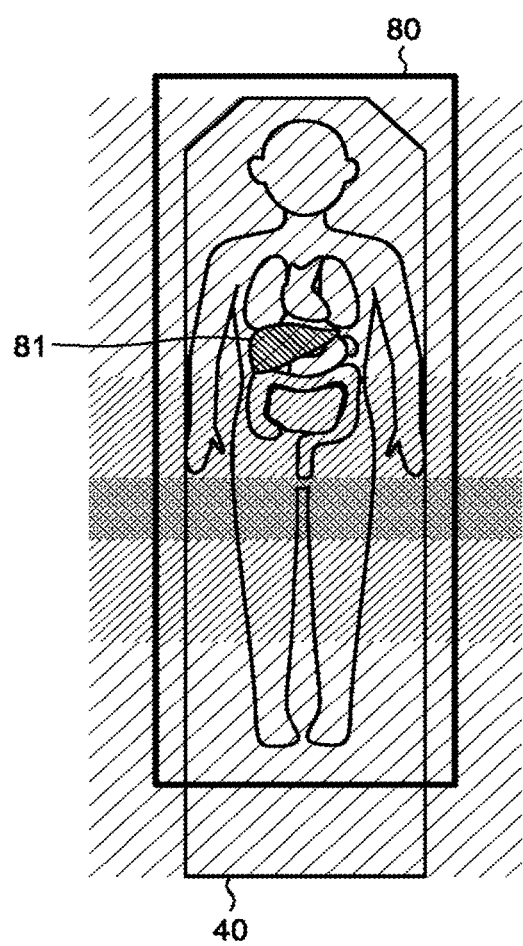
FIGS. 10A to 11B show one example of a display of a scano-image by the display control function according to the present embodiment.

FIGS. 10A to 11B show one example of a display of the scano-image by the display control function 37b according to the present embodiment. FIGS. 10A and 10B show an example when a scano-image 80 is displayed on the table top image 40 shown in FIGS. 8A and 8B, and FIGS. 11A and 11B show an example when the scano-image 80 is displayed on the table top image 40 shown in FIGS. 9A and 98. In the scano-image 80, a liver 81 or a small intestine 82, which is a subject of imaging, is drawn.

For example, as shown in FIGS. 10A to 11B, the display control function 37b displays the imaged scano-image 80 positioning on the table top image 40 based on a positional relationship between a position of the table top 21 defined using device coordinates in advance and a position on the image. Thus, the scano-image 80 is to be displayed in a size and direction appropriately adjusted according to the height and the direction of a subject, similarly to the simulation image 50 shown in FIGS. 8A to 9E.

When displaying the scano-image 80 also, the display control function 37b displays the graphic 60 that indicates a portion of the subject that is off an edge of the table top 21, for example, similarly to the example shown in FIG. 8B.

Figure 10B:
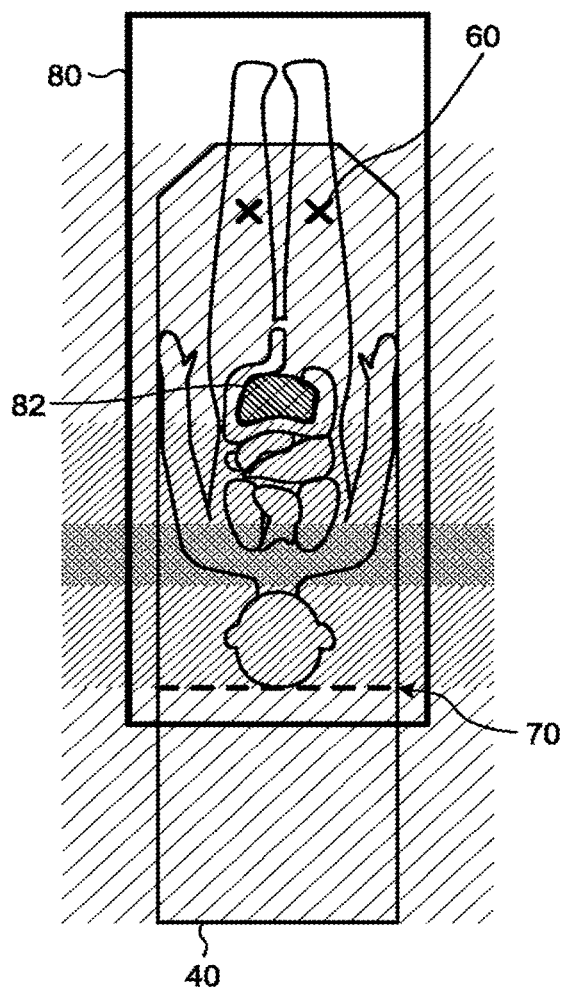
Figure 11A:
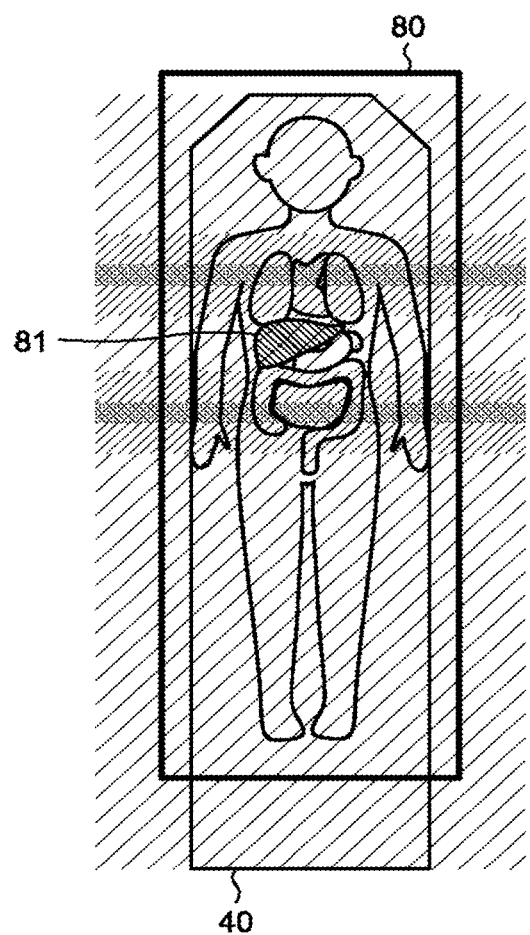
Figure 11B:
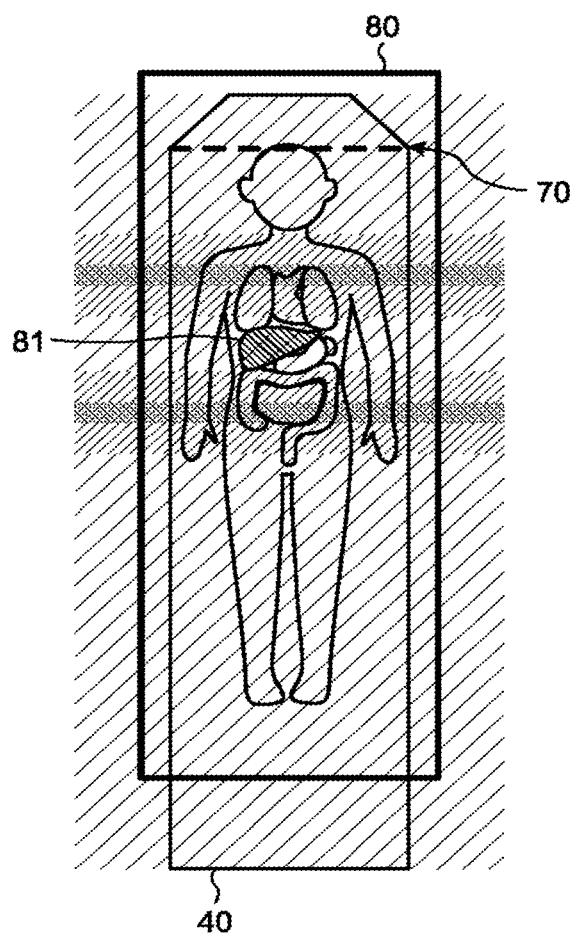

Moreover, as shown in FIG. 10B, when displaying the scano-image 80 also, the display control function 37b displays, at a position corresponding to a mark that is marked on the table top 21 in advance, the graphic 70 that indicates a position of the mark on the table top image 40, similarly to the example shown in FIGS. 8B and 9B.

As described, by displaying the scano-image 80 of a subject imaged for positioning of an imaging region to be imaged in a main imaging on the table top image 40 by the display control function 37b, it becomes possible for a radiologist or the like to judge more accurately whether portion of a subject of imaging is arranged at a position in which a vibration is small, when positioning the subject on the table top 21.

As described, the display control function 37b displays the information indicating the magnitude of vibration, associating with the positioning image of a subject.

Referring back to FIG. 7, when it is determined that the subject is not positioned appropriately by a radiologist or the like (step S7: NO), the imaging control function 37c images a scano-image again in response to a start instruction from the operator (step S5), and the display control function 37b again displays the imaged scano-image positioning or, the table top image 40 (step S6).

Thus, the radiologist or the like repeats imaging a scano-image until the subject is arranged at an appropriate position so that a portion of a subject of imaging is arranged at a position at which a vibration is small, referring to the scano image 80 displayed on the table top image 40.

When it is determined that the subject is appropriately positioned by the radiologist or the like (step S7: YES), the imaging control function 37c sets an imaging region for a main imaging, based on a position of an imaging region that is set on the scano-image by the operator (step S8).

Thereafter, the imaging control function 37c performs the main imaging of the subject in response to a start instruction from the operator (step S9).

FIG. 12 is a flowchart showing a processing procedure of main imaging that is performed by the imaging control function 27c according to the present embodiment.

For example, as shown in FIG. 12, when accepting a start instruction of main imaging from the operator step S10: YES), the imaging control function 37c first derives an attenuation time that is required until the magnitude of vibration that occurs at a position at which an X-ray intersects on the table top 21 when the table top 21 is moved to an imaging position becomes smaller than a predetermined value (step S11).

Thereafter, the imaging control function 37c derives a moving speed of the table top 21 with which the total of moving time that is required until the table top 21 is moved to the imaging position and the derived attenuation time is minimized (step S12). The imaging control function 37c then controls the bed driving device 22 to move the table top 21 to the imaging position at the derive moving speed (step S13).

Subsequently, at the time when the derived attenuation time has passed after the table top 21 is moved to the imaging position (step S14: YES), the imaging control function 37c starts imaging of the region of imaging that has been set using the scano-image (step S15). Thus, it becomes possible to start imaging automatically when a vibration that is occurring at a position at which an X-ray intersects on the table top 21 becomes smaller than a predetermined value.

Instead of automatically starting imaging, for example, the imaging control function 37c can give information indicating that the attenuation time has passed, when the derived attenuation time has passed. For example, the imaging control function 37c informs that the attenuation time has passed by displaying a message on the display 32. In this case, the imaging control function 37c accepts an operation to start imaging from the operator, and starts imaging taking the operation as a cue. Thus, it becomes possible to start imaging manually by the operator when a vibration that is occurring at a position at which an X-ray intersects on the table top 21 becomes smaller than a predetermined value.

As above, the processing performed by the display control function 37b and the imaging control function 37c has been explained. Steps S1, S5, S8, and S9 out of the steps shown in FIG. 7 are implemented, for example, by calling and executing a predetermined program corresponding to the imaging control function 37c by the processing circuitry 37 from the storage circuitry 35. Furthermore, steps S2, S3, and are implemented, for example, by calling and executing a predetermined program corresponding to the display control function 37b by the processing circuitry 37 from the storage circuitry 35. Moreover, the steps shown in FIG. 12 are implemented, for example, by calling and executing a predetermined program corresponding to the imaging control function 37c by the processing circuitry 37 from the storage circuitry 35.

Although the example in which imaging is performed moving the table top 21 to one imaging position has been explained, embodiments are not limited thereto. For example, when the step-and-shoot in which the conventional canning is performed at more than one imaging position while changing the position of the table top 21 at regular intervals is performed, the imaging control function 37c derives the attenuation time as described above, each time the table top 21 is moved to the respective imaging positions.

Furthermore, when the helical scanning in which the subject S is scanned helically rotating the rotating frame 15 while continuously moving the table top 21, for example, the imaging control function 37c can control the moving speed of the table top 21 and the rotating speed of the rotating frame 15 according to the magnitude of vibration that occurs at a position intersecting a path of an X-ray on the table top 21. In this case, for example, when a range in which a vibration is large intersects an X-ray on the table top 21, the imaging control function 37c controls the moving speed of the table top 21 and the rotating speed of the rotating frame 15 to be low compared to a range in which a vibration is small. For example, as shown in FIG. 4, when vibrations that occur on the table top 21 are divided into three ranges of "small vibration", "medium vibration", and "large vibration", the imaging control function 37c controls the moving speed of the table top 21 and the rotating speed of the rotating frame 15 to be low in the range of "medium vibration", compared to the range of "small vibration", and controls the moving speed of the table top 21 and the rotating speed of the rotating frame 15 to be low in the range of "large vibration" compared to the range of "medium vibration".

As described above, the X-ray CT apparatus 100 according to the present embodiment displays the information indicating the magnitude of vibration that occurs, when each position on the table top 21 is moved to a position intersecting a path of an X-ray, at the position, when positioning of a subject on the table top 21 is performed. This configuration enables a radiologist or the like to position a subject such that a portion of a subject of imaging is arranged at a position at which a vibration is small by referring to the displayed information, when positioning the subject on the table top 21.

Therefore, according to the present embodiment, it is possible to support appropriate positioning of a subject on a table top taking a vibration that occurs in the table top into account.

Note that the term "processor" signifies a central processing unit (CPU), a graphics processing unit (GPU), or circuitry such as an application specific integrated circuitry (ASIC), a programmable logic device (for example, a simple programmable logic device (SPLD), and a complex programmable logic device (CPLD)), and a field programmable gate array (FPGA). The processor implements the respective functions by reading and executing program that are stored in the storage circuitry 35. The programs can be configured to be directly installed in circuitry of the processor, instead of storing the programs in the storage circuitry. In this case, the processor implements the functions by reading and executing a program installed in the circuitry. The respective processors of the present embodiment are not limited to be configured as single circuitry per processor, but can be configured as one processor combining multiple independent circuitries to implement the functions.

Furthermore, the respective components of the respective devices illustrated in the above embodiment are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

According to at least one embodiment explained above, it is possible to support appropriate positioning of a subject on a table top, taking a vibration that occurs in the table top into account.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed-tomography (CT) apparatus comprising:
   an X-ray tube configured to generate an X-ray;
   a detector configured to detect the X-ray;
   a table top on which a subject is placed; and
   processing circuitry configured to
      control a moving mechanism to move the table top in a longitudinal direction, and
      display, on a display, a subject image corresponding to the subject, together with information indicating a plurality of magnitudes of vibration that respectively occur at a plurality of positions in the longitudinal direction on the table top, each magnitude of the plurality of magnitudes of vibration being a magnitude that occurs at the respective position when the position intersects a path of the X-ray, wherein the information is displayed along with a longitudinal direction of the displayed subject image.

2. The X-ray CT apparatus according to claim 1, wherein the processing circuitry is configured to display, according to an imaging condition, the information indicating the plurality of magnitudes of vibration that occur when imaging is performed based on the imaging condition.

3. The X-ray CT apparatus according to claim 2, wherein the processing circuitry is configured to display, according to an imaging condition relating to an orientation of the subject in the longitudinal direction when the subject is placed on the table top, the information indicating the plurality of magnitudes.

4. The X-ray CT apparatus according to claim 2, wherein the processing circuitry is configured to display, according to a weight of the subject, the information indicating the plurality of magnitudes of vibration that occurs when the subject of the weight is placed on the table top.

5. The X-ray CT apparatus according to claim 1, wherein the processing circuitry is further configured to display, on the display, information indicating a position to be a reference for positioning of the subject when the subject is to be placed on the table top.

6. The X-ray CT apparatus according to claim 1, wherein the processing circuitry is configured to display the information indicating the plurality of magnitudes of vibration, associating with, as the subject image, any one of a simulation image that expresses a shape of the subject in a simulated manner, and a positioning image of the subject.

7. The X-ray CT apparatus according to claim 1, wherein the processing circuitry is configured to display the information indicating the plurality of magnitudes of vibration associating with a simulation image of the table top.

8. The X-ray CT apparatus according to claim 1, wherein the processing circuitry is configured to display a table top image that expresses a shape of the table top, and that displays the information indicating the plurality of magnitudes of the vibration, associating with each position on the table top image.

9. The X-ray CT apparatus according to claim 8, wherein the subject image expresses a shape of the subject including a portion of a subject of imaging, and the processing circuitry is configured to display the subject image, positioning on the table top image.

10. The X-ray CT apparatus according to claim 9, wherein the processing circuitry is configured to display the subject image in a size according to a height of the subject.

11. The X-ray CT apparatus according to claim 9, wherein the processing circuitry is configured to show, when a part of the subject is off an edge of the table top when the subject image is positioned on the table top image, the part on the subject image in a recognizable manner.

12. The X-ray CT apparatus according to claim 1, wherein the processing circuitry is configured to display, as the subject image, a simulation image that expresses a shape of the subject in a simulated manner, such that a portion of a subject of imaging is arranged at a position at which a magnitude of the vibration is smaller than a predetermined value on the table top.

13. The X-ray CT apparatus according to claim 1, wherein the processing circuitry is configured to display, as the subject image, a positioning image of the subject that is imaged for positioning of an imaging region to be imaged in a main imaging.

14. The X-ray CT apparatus according to claim 1, wherein the processing circuitry is further configured to derive an attenuation time that is required until a magnitude of a vibration that occurs at a position at which the X-ray intersects on the table top when the table top is moved to an imaging position becomes smaller than a predetermined value, and to control imaging based on the attenuation time.

15. The X-ray CT apparatus according to claim 14, wherein
the processing circuitry is configured to control a moving speed of the table top such that a total of a moving time that is required until the table top is moved to an imaging position and the attenuation time is minimized.

16. The X-ray CT apparatus according to claim 14, wherein
the processing circuitry is configured to start the imaging when the attenuation time has passed since when the table top is moved to the imaging position.

17. The X-ray CT apparatus according to claim 14, wherein
the processing circuitry is configured to give information indicating that the attenuation time has passed, when the attenuation time has passed since when the table top is moved to the imaging position.

* * * * *